Figure 3A:
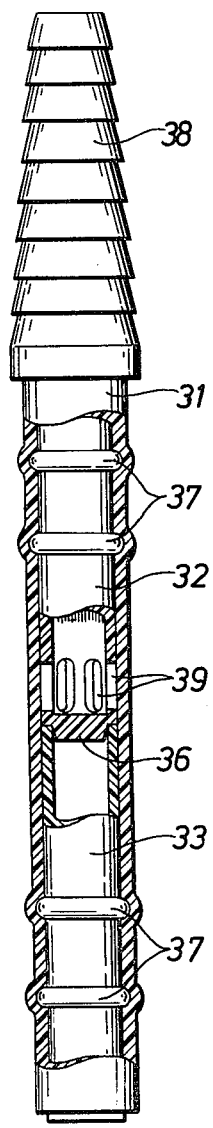

United States Patent [19]

Brendling

[11] 3,977,409
[45] Aug. 31, 1976

[54] TUBE VALVE
[76] Inventor: Lennart Ingvar Brendling, Axvagen 81, S-175 44 Jarfalla, Sweden
[22] Filed: Apr. 4, 1975
[21] Appl. No.: 565,300

[30] Foreign Application Priority Data
Apr. 8, 1974 Sweden.............................. 7404708

[52] U.S. Cl.............................. 128/349 R; 251/342
[51] Int. Cl.².................................... A61M 25/00
[58] Field of Search ..... 128/349 R, 349 RV, 350 R, 128/350 V, 351, 204, 274; 251/342

[56] References Cited
UNITED STATES PATENTS

| | | | |
|---|---|---|---|
| 2,706,101 | 4/1955 | Cantor | 251/342 |
| 2,918,718 | 1/1958 | Goldman | 128/350 R |
| 3,527,226 | 9/1970 | Hakim | 128/350 V |
| 3,827,439 | 8/1974 | Schulte | 128/350 V |

Primary Examiner—Louis G. Mancene
Assistant Examiner—Robert F. Cutting
Attorney, Agent, or Firm—William Anthony Drucker

[57] ABSTRACT

A tube valve for use in a catheter tube, the valve having two bodies inserted in the tube, the bodies filling the cross-sectional area of the tube. Each of the bodies is provided with at least one through opening which, in the closed position of the valve in which the two bodies are in coaxial alignment with one another, is closed by the tube or by the other body but can be exposed by elastic deformation of the tube while simultaneously displacing the bodies out of coaxial alignment.

7 Claims, 11 Drawing Figures

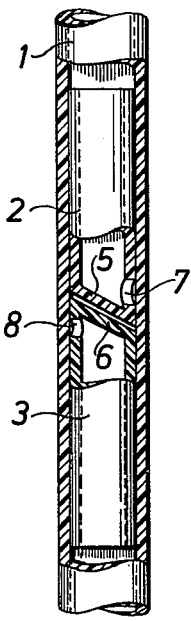
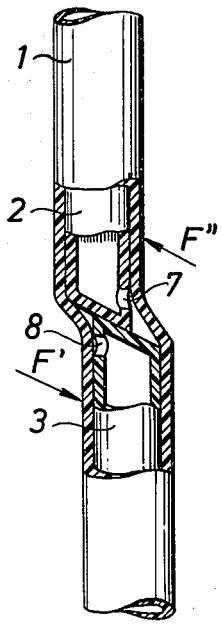
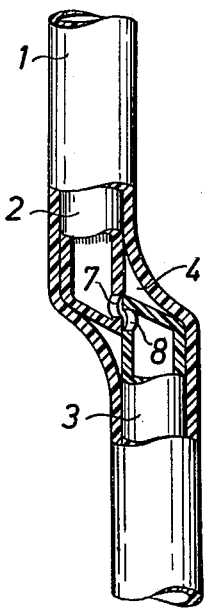
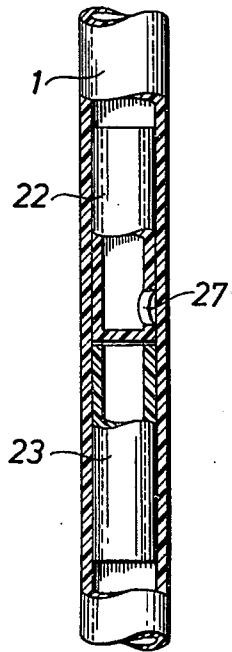
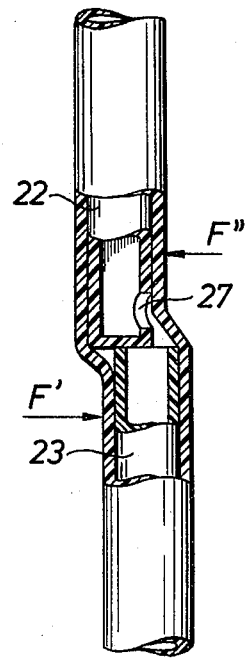
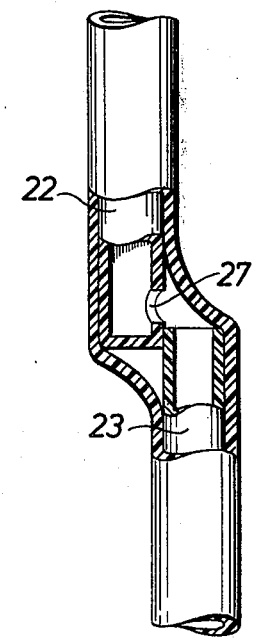

Fig. 4
Fig. 5
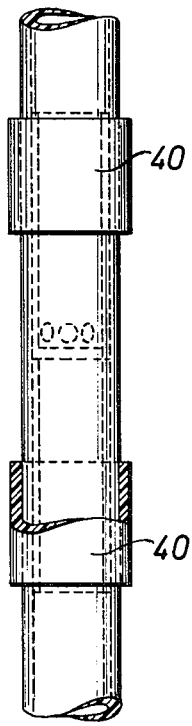
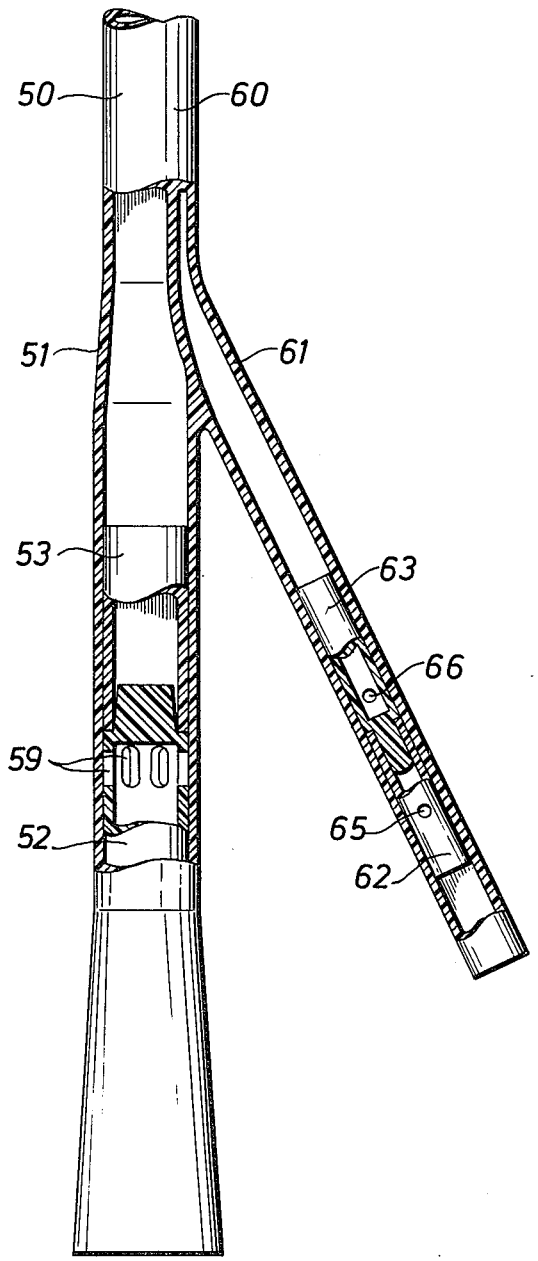

TUBE VALVE

The present invention relates to a tube valve for shutting-off the flow of a liquid or a gas through a tube. More particularly the invention relates to such valves for use with urine catheters and will hereinafter be described with reference to such catheters, although it will be understood that the invention is not restricted to such use but can be used in conjunction with other devices used within the medical field and industry.

The flow passage through urine catheters, which normally comprise tubes of a plastics or latex material, is usually closed by means of a conical plug which is normally made of a plastics material and which is adapted to be inserted into the catheter opening. Since the plug must be sterile before being used, used plugs must be discarded and replaced with a new, sterile plug each time the catheter is opened. Closure of urine catheters has also been effected by means of clips mounted in the outer surface of the catheter. Such clips, however, are relatively bulky and are liable to fasten in the clothing of persons using the catheter. Moreover, these clips sometimes have sharp edges and corners, which render said clips hazardous. When such clips are applied to a catheter for a long period of time, the catheter is liable to become deformed and if the force exerted by the clip is excessive, the inner surfaces of the catheter are liable to become tacky and stick together. One disadvantage encountered both with plastic plugs and tube clips is that they are difficult to manipulate by persons who have limited movement in their fingers.

These disadvantages are not encountered with the valve according to the invention. The valve according to the invention is permanently arranged within the tube and since the catheter, with the valve embodied therein, is sterilized when manufactured and since contamination of the valve does not readily occur upon the flow of urine from the bladder to the receptacle, the problem of sterilizing the valve is not encountered. Although the valve is mounted within the tube, the valve can be readily and quickly operated with the fingers from outside the tube, it being possible to open and close the valve, and particularly to close said valve, very rapidly. The valve is able to withstand relatively high pressures, the durability of the valve in this respect naturally depending upon the wall thickness of the tube and the quality of the tube material, and provides a positive seal in the closed position.

The valve according to the invention comprises two valve bodies arranged within the tube so as to fill the cross-sectional area of said tube. Each body has arranged therein at least one through opening which, in the closed position of the valve, i.e. when the two bodies are positioned co-axially in relation to one another, is closed by the tube or by the other body. The openings can be exposed, so as to provide free passage for fluid passing through the tube, by deforming the tube material whilst normally, at the same time, mutually displacing the bodies to a position in which they are no longer coaxial with one another.

Figure 3B:
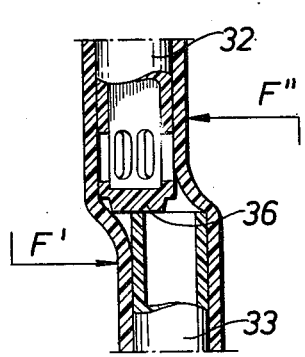
Figure 3C:
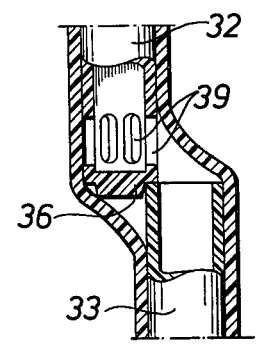

So that the invention will be more readily understood and further features thereof made apparent, embodiments of the invention will now be described with reference to the accompanying drawings, in which FIGS. 1a–c are cross-sectional views of a first embodiment in three different positions of the valve, FIGS. 2a–c are cross-sectional views of a second embodiment in three different positions of the valve, FIG. 3a is a cross-sectional view of a valve designed to operate as an openable catheter plug, FIGS. 3b and 3c are detail views of the embodiment shown in FIG. 3a corresponding to FIGS. 1b and 1c, FIG. 4 shows a fourth embodiment of the invention, and FIG. 5 shows an embodiment of a urine catheter provided with a valve according to the invention.

In FIG. 1 there is shown a tube 1, which may be a catheter tube. Inserted in the tube 1 are two, tubular plastic bodies 2 and 3 which are open at one end thereof but closed at the opposite end by means of inclined walls 5, 6. The plastic bodies are positioned in the tube with the closed, inclined end surfaces adjacent one another and with the open ends remote from one another. In the outer surface of each body adjacent the closed end thereof is provided a hole 7, 8.

In the position shown in FIG. 1a the valve is closed. As will be seen, the passage through the tube is closed by the inclined end walls, 5, 6 of the bodies 2, 3 and the holes 7, 8 are closed by the inner walls of the tube. In order to provide a reliable seal, the outer diameter of the bodies 2, 3 is conveniently somewhat larger than the inner diameter of the tube 1, so that the tube material is placed under tension when the bodies are inserted into the tube, thereby ensuring that the tube is held in abutment against the cylindrical surfaces of the valve bodies.

The valve is opened, for example, by gripping the bodies 2, 3 and moving said bodies laterally away from each other, as indicated by the force arrows F' and F'' shown in FIG. 1. Subsequent to moving the bodies laterally to an extent such that the inclined surfaces are free from each other as seen in the axial direction, the tension forces occurring in the tube 1 as the bodies are moved laterally will cause the bodies to be snapped over each other, as seen in FIG. 1c. The holes 7, 8 are then exposed and a cavity 4 is formed via which fluid can flow through the valve.

The valve is closed by pulling the ends of the tube of by moving the valve bodies axially away from one another. As soon as the valve bodies have been displaced in this way through a short distance they will snap back to the valve closing position, owing to the tension prevailing in the tube. The force required to open and close the valve may be determined by adjusting the tension in the tube material.

The valve shown in FIGS. 2a–c differs from the valve shown in FIGS. 1a–c insomuch as the ends of the valve bodies are straight and that one body, 23, has an open inner end while the other body, 22, has a hole 27 provided in the outer surface thereof, similar to the body 2 in the embodiment of FIGS. 1a–c. The valve shown in FIGS. 2a–c, however, is used and operates in the same manner as the valve shown in FIGS. 1a–c and hence will not be further described.

Since the valves described with reference to FIGS. 1a–c and FIGS. 2a–c are provided with only one peripheral hole in one or both valve bodies, the valve must be opened in a specific direction in order to expose said hole or holes. To overcome this a ring of holes may be arranged peripherally of the valve body, as is the case with the embodiments shown in FIGS. 3–5d hereinafter described. It is also possible to arrange one or more holes in the outer surface of a valve body provided with an open end (for example the body 23 in FIGS. 2a–c) thereby to improve the flow of fluid through the valve.

The valve shown in FIGS. 1 and 2 may also be momentarily opened by exerting sufficient pressure on one side of the tube (beneath or above the valve with respect to the embodiment of FIG. 1 and beneath the valve with respect to the embodiment of FIG. 2) in order to stretch the tube material and/or displace the bodies coaxially away from each other to an extent such that fluid is able to flow freely through the valve.

FIGS. 3a–c show an embodiment of a valve adapted to operate as an openable catheter plug. Inserted in a tube 31 are two tubular bodies 32, 33 of which one is provided with a connecting piece 38 projecting from one end of the tube, said connecting piece 38 being arranged for connection with the sleeve normally found on the majority of urine catheters. The two valve bodies 32, 33 are substantially the same as the valve bodies of the embodiment of FIGS. 2a–c, with the exception that the valve body 32 is provided with a ring of holes 39 instead of a single hole. In addition, the valve bodies are provided with peripheral flanges 37 for fixing said bodies in position and for maintaining the desired degree of tension in the tube. The upper valve body 32 is also provided with a shoulder 36 which may be cylindrical or frusto-conical and which extends into the end of the other valve body, thereby to serve to guide the valve bodies concentrically to one another, to prevent unintentional flexure of the tube at the position of the valve, and to form a support for the second valve body in the open position of the valve (FIG. 3c) so that said edge need not be moved up along the side surface of the valve body 32, which would otherwise restrict the flow of fluid through the valve.

When used, the valve shown in FIG. 3 is inserted into the sleeve of the urine catheter and is left in this position until the catheter is used. When the patient desires to urinate, the valve is opened in the before described manner, whereupon urine will be discharged. When the flow of urine ceases, the valve is closed for example by the patient.

Instead of the flanges of the FIG. 3a embodiment, rubber bands 40 or plastic shrink-bands may be used to fix the positions of the valve bodies, as shown in FIG. 4.

FIG. 5 shows an advantageous application of the invention, with the valve incorporated directly in the discharge portion of a catheter. In this instance, the catheter 50 is extended with a hose portion 51 corresponding to the length of the valve. The valve bodies 52, 53 have the same construction as the valve bodies 32, 33 in FIG. 3, although said bodies are not provided with flanges 37 and do not operate in conjunction with the connecting piece 38. As shown in FIG. 5, the closed end of the body 52 with the openings 59 is conveniently placed on the discharge side of the catheter and the other valve body 51 on the inlet side thereof. This positioning of the bodies is preferred, since a reverse positioning of the bodies may cause the openings 59 to become blocked with solid or semisolid substances present in the urine or which are formed upon contact of the urine with the tube material. The valve bodies shown in FIG. 5, may of course, be provided with flanges in the manner of the valve bodies shown in FIG. 3 or with bands in the manner of the embodiment shown in FIG. 4, in order to fix the positions of the valve bodies.

In the catheter shown in FIG. 5 there is arranged, in a normal manner, a further tube 60 which is narrower than the tube 50 and which is normally manufactured integral therewith. The tube 60 serves to enable a rubber bag or bladder attached to the inner end of the catheter to be inflated. The point of the catheter, together with the empty rubber bag is passed into the bladder and the bag filled with a specific volume of sterilized water or a therapeutically acceptable common salt solution, whereupon the tube 60 is closed. When the catheter is to be removed the bag is emptied by opening the tube 60. With the illustrated embodiment, the tube 60 is also provided with a valve 61, 62, 63 constructed in accordance with the invention, thereby enabling the filling and emptying of the bag to be effected in a simple manner. With present day constructions it is necessary, when emptying the bag, either to sever the tube 60 or to introduce a tubular probe into the valve. With the valve 61, 62, 63 according to the present invention it is only necessary to force liquid therein, for example by means of a syringe. In this way a through-passage is obtained between the openings 65, 66 of the valve of the valve bodies 62 and 63 as a result of the outward stretching of the tube under the pressure of the liquid injected thereinto. Emptying of the bag is effected by opening the valve in the aforedescribed manner.

In accordance with a further advantageous embodiment (not shown) the end of the tube 60 may be provided with two valves between which there is present a large cavity into which sterilized water may be passed, through the outer valve, during the manufacture of the catheter whereafter said outer valve is closed. Subsequent to inserting the catheter into the bladder, the inner valve is opened. By manually squeezing the bag filled with sterilized water, the water is forced up into the rubber bag inside the bladder. The inner valve is then closed. To remove the catheter, the two valves are opened whereupon the water runs out. Certain catheters are provided with inflated sterilized water bags to avoid the necessity of exerting manual pressure to force the water into the rubber bag located in the bladder. With catheters of this construction, an outer clip is placed in the position corresponding to the position of the inner valve during the manufacture of the catheter.

Although the invention has been described with reference to a number of embodiments thereof it will be understood that these embodiments are not restrictive of the invention, but that the invention can be applied to other devices used in industry and the medical field, for example, for the control of gas and liquid flow. The sealing construction of the valve does not change to any considerable extent, but different embodiments of the connection piece are conceivable. Similarly, different mechanical devices can be provided for opening and closing the valve.

The valve may also be used as a safety valve, since in the illustrated embodiments the valve can be opened simply by exerting a specific pressure thereon as mentioned above.

I claim:

1. A tube valve, particularly intended for incorporation in a catheter tube, characterized in that said valve comprises two valve bodies inserted in the tube, said bodies filling the cross-sectional area of said tube and each of said bodies being provided with at least one through opening which, in the closed position of the valve in which the two bodies are in coaxial alignment with one another, is closed by the tube or by the other body but can be exposed by elastic deformation of the tube whilst simultaneously displacing said bodies out of said coaxial alignment.

2. A valve according to claim 1, wherein the two bodies are closed at the opposing ends thereof and have peripheral openings which in said position of coaxial alignment are closed by the tube.

3. A valve according to claim 1, wherein one body is axially open at its end facing the second body, said end being closed, and wherein said second body or both bodies have peripheral openings which are closed by the tube in said position of coaxial alignment.

4. A valve according to claim 3, wherein said body having the closed end is provided with a shoulder for insertion into the open end of said second body, said shoulder being intended to fix the axial position of the bodies.

5. A valve according to claim 1, wherein at least one body is provided with a connecting piece for connection to a hose.

6. A valve according to claim 1, wherein said bodies have on their peripheral surfaces fixing means in the form of flanges or similar projections.

7. A valve according to claim 1, wherein said fixing means, for example in the form of rubber bands, are mounted externally of the tube around said bodies.

* * * * *